US009861828B2

(12) United States Patent
Norton et al.

(10) Patent No.: US 9,861,828 B2
(45) Date of Patent: *Jan. 9, 2018

(54) MONITORING MULTI-CELL POWER SOURCE OF AN IMPLANTABLE MEDICAL DEVICE

(71) Applicant: Medtronic, Inc., Minneapolis, MN (US)

(72) Inventors: John D Norton, St. Paul, MN (US); Craig L Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/695,826

(22) Filed: Apr. 24, 2015

(65) Prior Publication Data
US 2016/0067510 A1 Mar. 10, 2016

Related U.S. Application Data

(60) Provisional application No. 62/139,883, filed on Mar. 30, 2015, provisional application No. 62/084,163, (Continued)

(51) Int. Cl.
*A61N 1/39* (2006.01)
*A61N 1/378* (2006.01)

(52) U.S. Cl.
CPC ......... *A61N 1/3975* (2013.01); *A61N 1/3925* (2013.01); *A61N 1/3956* (2013.01)

(58) Field of Classification Search
CPC .... A61N 1/378; A61N 1/3975; A61N 1/3937; A61N 1/3956; H01M 10/4257
See application file for complete search history.

(56) References Cited

U.S. PATENT DOCUMENTS 2,830,123 A 4/1958 Trousdale
3,222,592 A 12/1965 Kellogg
(Continued)

FOREIGN PATENT DOCUMENTS

EP 0780918 A1 9/1996
EP 0920115 B1 11/2004
(Continued)

OTHER PUBLICATIONS

C00006924.WOU3 (PCT/US2015/042329) PCT Notification of Transmittal of the International Search Report and the Written Opinion of the International Searching Authority, mailed Jan. 26, 2016, 13 pages.
(Continued)

*Primary Examiner* — William Levicky

(57) ABSTRACT

An implantable medical device includes a low-power circuit and a multi-cell power source. The cells of the power source are coupled in a parallel configuration. The implantable medical device includes both a low power circuit and a high power circuit that are coupled between the first and second cells. An isolation circuit is coupled to the first cell and the second cell in a safe parallel orientation and the first and second cells are configured in a first configuration to deliver energy to the low power circuit segment and in a second configuration that is different from the first configuration to deliver energy to the high power circuit segment. A monitoring circuit is coupled to the power source and operable to evaluate the first cell and the second cell to detect a fault condition associated with at least one of the first and second cells.

21 Claims, 10 Drawing Sheets

Related U.S. Application Data filed on Nov. 25, 2014, provisional application No. 62/047,136, filed on Sep. 8, 2014, provisional application No. 62/047,128, filed on Sep. 8, 2014.

(56) References Cited

U.S. PATENT DOCUMENTS

| | | |
|---|---|---|
| 3,697,808 A | 10/1972 | Lee |
| 3,770,504 A | 11/1973 | Bergum |
| 3,824,129 A | 7/1974 | Fagan |
| 3,888,260 A | 6/1975 | Fischell |
| 4,119,720 A | 10/1978 | Hardtmann |
| 4,204,036 A | 5/1980 | Cohen et al. |
| 4,217,645 A | 8/1980 | Barry et al. |
| 4,375,817 A | 3/1983 | Engle et al. |
| 4,595,009 A | 6/1986 | Leinders |
| 4,800,883 A | 1/1989 | Winstrom |
| 4,860,185 A | 8/1989 | Brewer |
| 4,964,877 A | 10/1990 | Keister et al. |
| 5,137,020 A | 8/1992 | Wayne |
| 5,147,737 A | 9/1992 | Post et al. |
| 5,163,427 A | 11/1992 | Keimel |
| 5,178,140 A | 1/1993 | Ibrahim |
| 5,188,105 A | 2/1993 | Keimel |
| 5,221,453 A | 6/1993 | Crespi |
| 5,235,979 A | 8/1993 | Adams |
| 5,250,373 A | 10/1993 | Muffoletto et al. |
| 5,251,624 A | 10/1993 | Bocek et al. |
| 5,285,779 A | 2/1994 | Cameron |
| 5,306,581 A | 4/1994 | Taylor et al. |
| 5,312,458 A | 5/1994 | Muffoletto et al. |
| 5,360,435 A | 11/1994 | DeGroot |
| 5,372,605 A | 12/1994 | Adams et al. |
| 5,383,907 A | 1/1995 | Kroll |
| 5,434,017 A | 7/1995 | Berkowitz et al. |
| 5,439,760 A | 8/1995 | Howard et al. |
| 5,447,522 A | 9/1995 | Chang |
| 5,458,977 A | 10/1995 | Hosokawa et al. |
| 5,470,341 A | 11/1995 | Kuehn et al. |
| 5,543,773 A | 8/1996 | Evans |
| 5,545,181 A | 8/1996 | Jacobson et al. |
| 5,549,646 A | 8/1996 | Katz et al. |
| 5,549,717 A | 8/1996 | Takeuchi et al. |
| 5,591,212 A | 1/1997 | Keimel |
| 5,591,218 A | 1/1997 | Jacobson |
| 5,626,619 A | 5/1997 | Jacobson et al. |
| 5,656,966 A | 8/1997 | Wilmot et al. |
| 5,674,248 A | 10/1997 | Kroll et al. |
| 5,700,280 A | 12/1997 | Silvian |
| 5,702,431 A | 12/1997 | Wang |
| 5,814,075 A | 9/1998 | Kroll |
| 5,825,079 A | 10/1998 | Metzler et al. |
| 5,836,973 A | 11/1998 | Kroll |
| 5,994,880 A | 11/1999 | Dropps |
| 6,008,625 A | 12/1999 | Gan et al. |
| 6,016,002 A | 1/2000 | Chen |
| 6,038,473 A | 3/2000 | Olson et al. |
| 6,040,082 A | 3/2000 | Haas et al. |
| 6,044,295 A | 3/2000 | Pilz et al. |
| 6,081,095 A | 6/2000 | Tamura et al. |
| 6,087,809 A | 7/2000 | Gan et al. |
| 6,094,597 A | 7/2000 | Wold |
| 6,163,723 A | 12/2000 | Roberts et al. |
| 6,209,764 B1 | 4/2001 | Hartlaub |
| 6,238,813 B1 | 5/2001 | Maile et al. |
| 6,240,318 B1 | 5/2001 | Phillips |
| 6,269,266 B1 | 7/2001 | Leysieffer |
| 6,366,817 B1 | 4/2002 | Kung |
| 6,420,757 B1 | 7/2002 | Metzler |
| 6,426,628 B1 | 7/2002 | Palm |
| 6,438,420 B1 | 8/2002 | Thompson |
| 6,490,484 B2 | 12/2002 | Dooley et al. |
| 6,549,807 B1 | 4/2003 | Kroll |
| 6,552,511 B1 | 4/2003 | Fayram |
| 6,627,337 B2 | 9/2003 | Gan et al. |
| 6,650,942 B2 | 11/2003 | Howard et al. |
| 6,671,552 B2 | 12/2003 | Merritt |
| 6,744,152 B2 | 6/2004 | Kroll |
| 6,777,908 B2 | 8/2004 | Thorne et al. |
| 6,909,915 B2 | 6/2005 | Greatbatch |
| 6,971,391 B1 | 12/2005 | Wang |
| 7,020,519 B2 | 3/2006 | Greatbatch |
| 7,079,893 B2 | 7/2006 | Greatbatch |
| 7,103,404 B2 | 9/2006 | Stadler |
| 7,120,492 B2 | 10/2006 | Iverson et al. |
| 7,136,701 B2 | 11/2006 | Greatbatch |
| 7,191,008 B2 | 3/2007 | Schmidt et al. |
| 7,209,784 B2 | 4/2007 | Schmidt |
| 7,225,018 B2 | 5/2007 | Iverson et al. |
| 7,337,001 B2 | 2/2008 | Schmidt |
| 7,598,706 B2 | 10/2009 | Koski et al. |
| 7,671,714 B2 | 3/2010 | Tiemeijer |
| 7,783,357 B2 | 8/2010 | Brink |
| 7,956,714 B2 | 6/2011 | Ackermann |
| 7,962,212 B2 | 6/2011 | Signoff |
| 8,086,312 B2 | 12/2011 | Nielsen |
| 8,120,262 B2 | 2/2012 | Lee et al. |
| 8,120,321 B2 | 2/2012 | Vezzini et al. |
| 8,130,066 B2 | 3/2012 | Dunlap |
| 8,183,833 B2 | 5/2012 | Kobayashi |
| 8,209,032 B2 | 6/2012 | Ebert |
| 8,228,025 B2 | 7/2012 | Ho et al. |
| 8,447,414 B2 | 5/2013 | Johnson |
| 8,452,395 B2 | 5/2013 | Crespi |
| 8,452,399 B2 | 5/2013 | Wanasek |
| 8,498,716 B2 | 7/2013 | Chen |
| 8,502,502 B2 | 8/2013 | Huang |
| 8,508,191 B2 | 8/2013 | Kim et al. |
| 8,532,785 B1 | 9/2013 | Crutchfield et al. |
| 8,536,824 B2 | 9/2013 | St-Jacques |
| 8,588,913 B2 | 11/2013 | Signoff |
| 8,598,844 B2 | 12/2013 | Densham |
| 8,612,167 B2 | 12/2013 | Schmidt |
| 8,649,862 B2 | 2/2014 | Ludwig |
| 8,901,888 B1 | 12/2014 | Beckman |
| 8,914,105 B2 | 12/2014 | Wanasek |
| 8,928,441 B2 | 1/2015 | Prabhakaran |
| 8,972,005 B2 | 3/2015 | Rasmussen et al. |
| 2002/0013610 A1 | 1/2002 | Vane et al. |
| 2003/0042437 A1 | 3/2003 | Worley et al. |
| 2003/0058659 A1 | 3/2003 | Klinkowstein |
| 2003/0160588 A1 | 8/2003 | Kroll |
| 2003/0198866 A1 | 10/2003 | Tanjou et al. |
| 2004/0044371 A1 | 3/2004 | Tamura et al. |
| 2004/0147972 A1 | 7/2004 | Greatbatch et al. |
| 2004/0193227 A1 | 9/2004 | Schmidt |
| 2004/0267322 A1 | 12/2004 | Kavounas et al. |
| 2005/0288743 A1 | 12/2005 | Ahn |
| 2006/0100674 A1 | 5/2006 | Molin |
| 2006/0111752 A1 | 5/2006 | Greatbatch |
| 2006/0129192 A1 | 6/2006 | Greatbatch |
| 2006/0167496 A1 | 7/2006 | Nelson |
| 2006/0195148 A1 | 8/2006 | Norton et al. |
| 2006/0276851 A1 | 12/2006 | Schmidt |
| 2007/0001796 A1 | 1/2007 | Waffenschmidt et al. |
| 2007/0150019 A1 | 6/2007 | Youker |
| 2007/0203528 A1 | 8/2007 | Vernon |
| 2007/0216368 A1 | 9/2007 | Chandler et al. |
| 2007/0254212 A1 | 11/2007 | Viavattine |
| 2008/0015644 A1 | 1/2008 | Julian et al. |
| 2008/0097544 A1* | 4/2008 | Gandhi ............... A61N 1/3708 607/29 |
| 2008/0114241 A1 | 5/2008 | Randall et al. |
| 2008/0223381 A1* | 9/2008 | Schmidt ............... A61N 1/3956 128/899 |
| 2008/0238205 A1 | 10/2008 | Lee |
| 2009/0157130 A1 | 6/2009 | Ideker et al. |
| 2009/0157131 A1 | 6/2009 | Ideker et al. |
| 2009/0322155 A1 | 12/2009 | Oh |
| 2010/0046251 A1 | 2/2010 | Kyono |
| 2010/0114248 A1 | 5/2010 | Donofrio et al. |
| 2011/0003182 A1 | 1/2011 | Zhu |
| 2011/0127926 A1 | 6/2011 | Samejima et al. |
| 2011/0149613 A1 | 6/2011 | Lanni |
| 2011/0179637 A1 | 7/2011 | Eberman et al. |

(56) References Cited

U.S. PATENT DOCUMENTS

| 2011/0184483 | A1 | 7/2011 | Norton |
| 2011/0213434 | A1 | 9/2011 | Signoff |
| 2012/0191150 | A1 | 7/2012 | Kameli |
| 2012/0265266 | A1 | 10/2012 | Colborn |
| 2012/0319495 | A1 | 12/2012 | Muller |
| 2013/0088202 | A1 | 4/2013 | Kamata et al. |
| 2013/0245718 | A1 | 9/2013 | Birkholz et al. |
| 2014/0266102 | A1 | 9/2014 | Mikolajczak |
| 2014/0353567 | A1 | 12/2014 | Wang et al. |
| 2015/0327963 | A1 | 11/2015 | Fregoso et al. |
| 2016/0067506 | A1 | 3/2016 | Crutchfield et al. |
| 2016/0067507 | A1 | 3/2016 | Cabelka et al. |
| 2016/0067508 | A1 | 3/2016 | Boone et al. |
| 2016/0067509 | A1 | 3/2016 | Meador et al. |
| 2016/0067510 | A1 | 3/2016 | Norton et al. |
| 2016/0067512 | A1 | 3/2016 | Norton et al. |
| 2016/0067513 | A1 | 3/2016 | Crutchfield et al. |

FOREIGN PATENT DOCUMENTS

| WO | 94/02202 | A1 | 2/1994 |
| WO | 94/22022 | A2 | 8/1994 |
| WO | 2006/058028 | A2 | 6/2006 |
| WO | 2007/145460 | A1 | 12/2007 |

OTHER PUBLICATIONS

"Active Cell Balancing in Battery Packs", by Stanislav Arendarik, Freescale Semiconductor, Inc., 2012, 8 pages.

C00006865.WOU3 (PCT/US2015/042328) PCT Notification of Transmittal of the International Search Report and the Written Opinion of the International Searching Authority, mailed Sep. 30, 2015, 9 pages.

C00006923.WOU3 (PCT/US2015/042331) PCT Notification of Transmittal of the International Search Report and the Written Opinion of the International Searching Authority, mailed Nov. 5, 2015, 11 pages.

C00007044.WOU3 (PCT/US2015/042332) PCT Notification of Transmittal of the International Search Report and the Written Opinion of the International Searching Authority, mailed Oct. 30, 2015, 11 pages.

Http://www.rmcybernetics.com/shop/matching-transformer, 5 pages, printed Sep. 7, 2016.

Non-Final Office Action for related U.S. Appl. No. 14/695,630 mailed on Apr. 19, 2016 (9 pages).

"Design of a Current Controlled Defibrillator" Jonsson, Jorgensen, A Masters Thesis, Department of Industrial Electrical Engineering and Automation, Lund Institute of Technology (Nov. 23, 2004).

"Impedance Matching Transformer Kit, Ideal for Induction Heating and Power Inverters", RMCybernetics, http://www.rmcybernetics.com/shop/matching-transformer (accessed May 16, 2014).

* cited by examiner

MONITORING MULTI-CELL POWER SOURCE OF AN IMPLANTABLE MEDICAL DEVICE

CROSS-REFERENCE TO RELATED APPLICATIONS

This application claims the benefit of U.S. Provisional Application Nos. 62/139,883, filed on Mar. 30, 2015, 62/084,163, filed on Nov. 25, 2014, 62/047,136, filed on Sep. 8, 2014, and 62/047,128, filed on Sep. 8, 2014. The disclosures of the above applications are incorporated herein by reference in their entireties.

The present application is related to co-pending and commonly-assigned U.S. patent application Ser. No. 14/695,264 which is entitled Multi-Primary Transformer Charging Circuits for Implantable Medical Devices; U.S. patent application Ser. No. 14/695,309, which is entitled Implantable Medical Devices Having Multi-Cell Power Sources; U.S. patent application Ser. No. 14/695,447, which is entitled Multiple Transformer Charging Circuits for Implantable Medical Devices; U.S. patent application Ser. No. 14/695,630, which is entitled Transformer-Based Charging Circuits for Implantable Medical Devices; U.S. patent application Ser. No. 14/695,948, which is entitled Implantable Medical Devices Having Multi-Cell Power Sources; and U.S. patent application Ser. No. 14/695,887, which is entitled Transthoracic Protection Circuit for Implantable Medical Devices, all of which are filed concurrently herewith and all of which are incorporated herein by reference in their entireties.

FIELD

The present disclosure relates to body implantable medical devices and, more particularly to circuits and techniques implemented in an implantable medical device to provide an electrical therapeutic output.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with implantable medical devices.

Implantable medical electrical leads are used with a wide variety of these implantable medical devices. The medical leads may be configured to allow electrodes to be positioned at desired cardiac locations so that the device can monitor and/or deliver stimulation therapy to the desired locations. For example, electrodes on implantable leads may detect electrical signals within a patient, such as an electrocardiogram, in addition to delivering electrical stimulation.

Currently, ICD's use endocardial or epicardial leads which extend from the ICD housing through the venous system to the heart. Electrodes positioned in or adjacent to the heart by the leads are used for pacing and sensing functions. Cardioversion and defibrillation shocks are generally applied between a coil electrode carried by one of the leads and the ICD housing, which acts as an active can electrode.

A subcutaneous implantable cardioverter defibrillator (SubQ ICD) differs from the more commonly used ICD's in that the housing and leads are typically implanted subcutaneously such that the sensing and therapy are accomplished subcutaneously. The SubQ ICD does not require leads to be placed in the heart or in contact with the heart. Instead, the SubQ ICD makes use of one or more electrodes on the housing, together with a subcutaneous lead that carries a defibrillation coil electrode and a sensing electrode.

The implantable medical devices are typically battery powered and often utilize capacitors or other electrical charge storage components to hold an electrical output to be made available to a patient. Due to the nature of defibrillation therapy or other high voltage therapy, it is not practical for the implantable medical device to supply the energy upon instantaneous demand by drawing from the power source. Instead, additional circuitry is provided to transfer and store the energy from the power source to accumulate a desired voltage level.

However, the placement of the SubQ ICD lead(s) and electrode(s) outside the heart presents a challenge to generating sufficient energy levels that are required to deliver appropriate therapy. As described herein, the present disclosure addresses the need in art to provide circuitry and techniques for generating appropriate electrical stimulation therapy in a SubQ ICD system.

SUMMARY

In accordance with aspects of this disclosure, circuits and techniques implemented in an implantable medical device are provided for generating an electrical stimulation therapy from a multi-cell power source. Such electrical stimulation therapy exhibits an output having a higher voltage than the voltage available directly from the battery or a higher current than the current available directly from the battery.

In accordance with some embodiments, the implantable medical device comprises operational circuitry having a low power circuit segment and a high power circuit segment, a power source having at least first and second cells coupled to the operational circuitry, an isolation circuit connected to the first and second cells and operable to couple the first and second cells in a safe parallel orientation, with the first and second cells being configured in a first configuration to deliver energy to the low power circuit segment and in a second configuration that is different from the first configuration to deliver energy to the high power circuit segment, and a monitoring circuit coupled to the power source and operable to compute a first value corresponding to a parameter of the first cell and a second value corresponding to the parameter of the second cell, with the monitoring circuit being configured to evaluate the first value and the second value to detect a fault condition associated with at least one of the first and second cells.

In further aspects of the embodiments of the present disclosure, the isolation circuit is configured having an impedance that permits the isolation circuit to be bypassed during delivery of energy from the first and second cells to the high power circuit segment.

In further aspects of the embodiments of the present disclosure, the monitoring circuit measures a current flowing through each of the first and second cells to compute the first and second values.

In further aspects of the embodiments of the present disclosure, the monitoring circuit measures an output voltage of each of the first and second cells to compute the first and second values.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

In accordance with embodiments of the present disclosure, a power source of an implantable medical device is evaluated to assess the relative discharge rate of a power source. As used in this disclosure, the power source refers to energy storage devices such as a stand-alone battery that may non-rechargeable or a rechargeable storage battery. The disclosure contemplates a power source having at least two cells (multi-cell battery). As used in this disclosure, the term "cell" refers to a battery cell which, as is understood in the art, includes an anode terminal and a cathode terminal. An example of a battery cell is set forth in commonly assigned U.S. Patent Application No. US 2011/0179637 "Implantable Medical Devices with Low Volume Batteries, and Systems", to Norton which is incorporated herein by reference. For simplicity, the multi-cell power source or multi-cell battery will hereinafter be referred to as a "battery". The disclosure describes techniques for obtaining a parameter indicative of the rate of the discharge of the power source, or the residual energy of the power source, including the remaining capacity in the individual cells of the power source. The residual energy (charge) in each of the cells may facilitate the identification of a fault condition associated with the power source. In addition, the remaining longevity will provide an indication of the remaining useful life of the power source.

Figure 1:
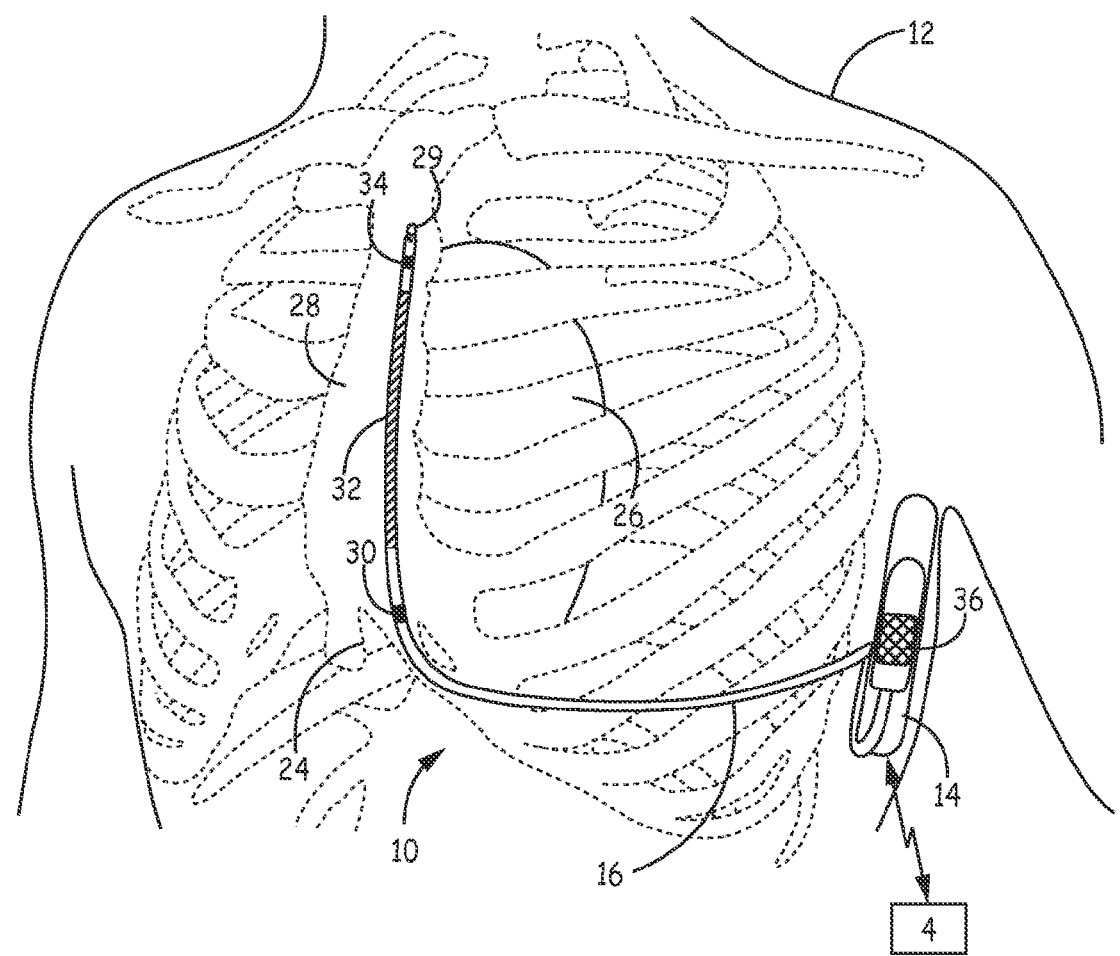
FIG. 1 is a front view of a patient implanted with an implantable cardiac system.

FIG. 1 is a conceptual diagram of a patient 12 implanted with an example extravascular cardiac defibrillation system 10. In the example illustrated in FIG. 1, extravascular cardiac defibrillation system 10 is an implanted subcutaneous defibrillation system for purposes of illustration.

Extravascular cardiac defibrillation system 10 includes an implantable medical device such as implantable cardiac defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24 defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

ICD 14 may interact with an external device 4 such as a patient programmer or a clinician programmer via a 2-way telemetry link. Such a programmer communicates with ICD 14 via telemetry as is known in the art. The programmer 4 may thereby establish a telemetry session with ICD 14 to provide programs, instructions, parameters, data, and other information to ICD 14, and to likewise receive status, data, parameters, programs, and other information from the ICD 14. Status information received from the ICD 14 may include data about the remaining longevity of the power source based on the amount of charge that has thus far been delivered by the battery and consumed by the ICD 14 as compared to when the battery was in the full-charged state ("battery capacity"). Status information may also include an "Elective Replacement Indicator" (ERI) to indicate when surgery must be scheduled to replace ICD 14. Status may also include an "End of Life" (EOL), which is activated to signify end-of-battery life.

Defibrillation lead 16 is placed along sternum 28 such that a therapy vector between defibrillation electrode 32 and a second electrode (such as a housing or can electrode 36 of ICD 14 or an electrode placed on a second lead) is substantially across the ventricle of heart 26. The therapy vector may, in one example, be viewed as a line that extends from a point on the defibrillation electrode 32 to a point on the housing or can electrode 36 of ICD 14. In another example, defibrillation lead 16 may be placed along sternum 28 such that a therapy vector between defibrillation electrode 32 and a housing or can electrode 36 of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 32, 34, and 30, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing that forms a hermetic seal that protects components within ICD 14. The housing of ICD 14 may be formed of a conductive material, such as titanium or other biocompatible conductive material or a combination of conductive and non-conductive materials. In some instances, the housing of ICD 14 functions as an electrode (sometimes referred to as a housing electrode or can electrode) that is used in combination with one of electrodes 32, 34, or 30 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. The housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 32, 34, and 30. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 32, 34 and 30, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 32, 34 and 30. In other words, each of the one or more elongated electrical conductors contained within the lead body of defibrillation lead 16 may engage with respective ones of electrodes 32, 34 and 30. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 32, 34 and 30 and transmit sensed electrical signals from one or more of electrodes 32, 34 and 30 to the sensing module within ICD 14.

ICD 14 may sense electrical activity of heart 26 via one or more sensing vectors that include combinations of electrodes 34 and 30 and a housing or can electrode 36 of ICD 14. For example, ICD 14 may obtain electrical signals sensed using a sensing vector between electrodes 34 and 30, obtain electrical signals sensed using a sensing vector between electrode 34 and the conductive housing or can electrode 36 of ICD 14, obtain electrical signals sensed using a sensing vector between electrode 30 and the conductive housing or can electrode 36 of ICD 14, or a combination thereof. In some instances, ICD 14 may even sense cardiac electrical signals using a sensing vector that includes defibrillation electrode 32, such as a sensing vector between defibrillation electrode 32 and one of electrodes 34 or 30, or a sensing vector between defibrillation electrode 32 and the housing or can electrode 36 of ICD 14.

ICD 14 may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 32 of defibrillation lead 16 and the housing/can electrode. Defibrillation electrode 32 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 34 and 30 and/or the housing/can electrode. Electrodes 34 and 30 may comprise ring electrodes, hemispherical electrodes, coil electrodes, helix electrodes, segmented electrodes, directional electrodes, or other types of electrodes, or combination thereof. Electrodes 34 and 30 may be the same type of electrodes or different types of electrodes, although in the example of FIG. 1 both electrodes 34 and 30 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29. In this case, defibrillation lead 16 may be connected to or secured to an implant tool via an interference fit as will be described in more detail herein. An interference fit, sometimes also referred to as a friction fit, is a fastening between two parts which is achieved by friction after the parts are pushed together, rather than by any other means of fastening.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 30 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs and/or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the sub-xiphoid or inferior xiphoid area, near the apex of the heart, or other location not in direct contact with heart 26 and not subcutaneous. In still further instances, the implant tools described herein may be utilized to implant the lead at a pericardial or epicardial location outside the heart 26. Moreover, implant tools such as those described herein may be used to implant non-cardiac leads in other locations within patient 12.

Figure 2:
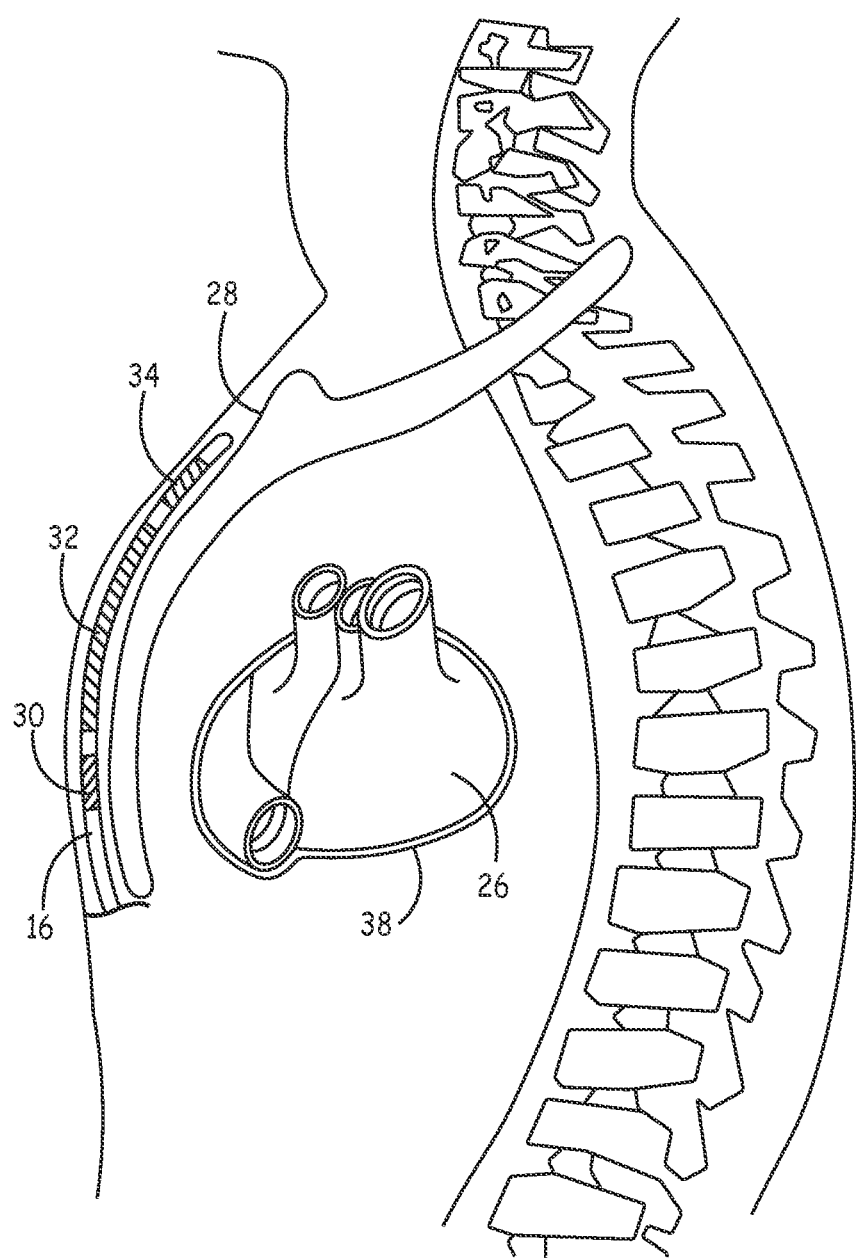
FIG. 2 is a side view the patient implanted with an implantable cardiac system.
Figure 3:
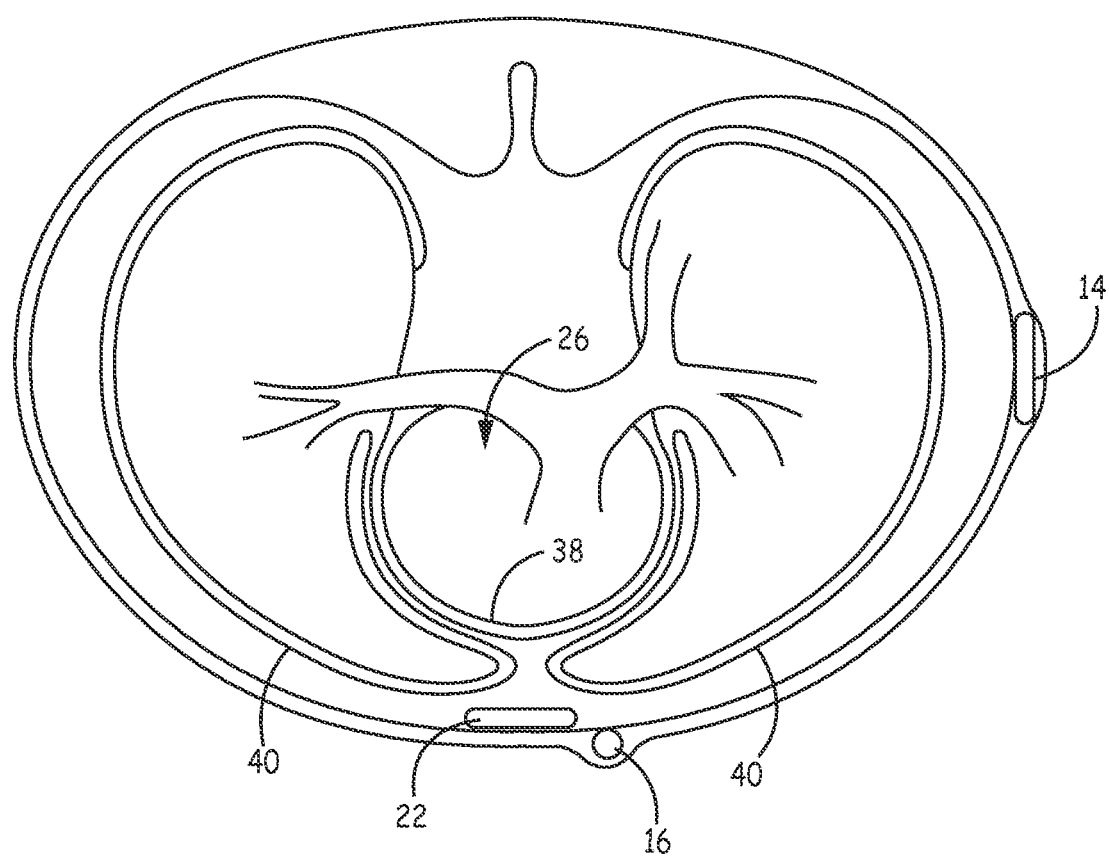
FIG. 3 is a transverse view of the patient implanted with an implantable cardiac system.

In an example, lead 16 may be placed in the mediastinum and, more particularly, in the anterior mediastinum. The anterior mediastinum is bounded laterally by pleurae 40, posteriorly by pericardium 38, and anteriorly by sternum 22. Lead 16 may be implanted within the mediastinum such that one or more electrodes 32 and 34 are located over a cardiac silhouette of the ventricle as observed via fluoroscopy. In the example illustrated in FIGS. 1-3, lead 16 is located substantially centered under sternum 22. In other instances, however, lead 16 may be implanted such that it is offset laterally from the center of sternum 22. Although described herein as being implanted in the substernal space, the mediastinum, or the anterior mediastinum, lead 16 may be implanted in other extra-pericardial locations.

Electrodes 30, 32, and 34 may comprise ring electrodes, hemispherical electrodes, coil electrodes, helical electrodes, ribbon electrodes, or other types of electrodes, or combinations thereof. Electrodes 30, 32 and 34 may be the same type of electrodes or different types of electrodes. In the example illustrated in FIGS. 1-3 electrode 34 is a coil electrode and electrodes 30 and 34 are ring, or hemispherical electrodes.

Figure 4:
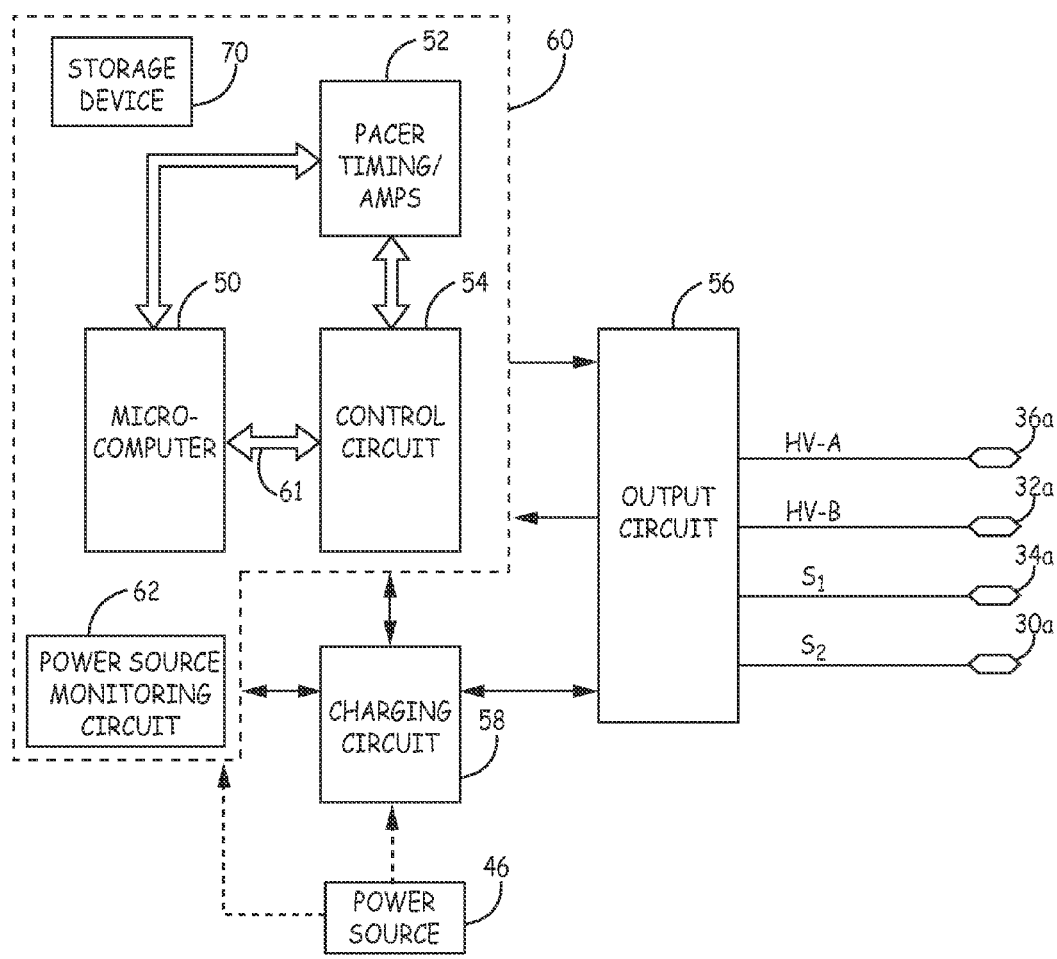
FIG. 4 depicts a schematic diagram of an embodiment of operational circuitry included in an implantable cardiac defibrillator of the cardiac system of FIGS. 1-3.

FIG. 4 is a schematic diagram of operational circuitry 48 included in ICD 14 according to an embodiment of the present disclosure. It is understood that the system of FIG. 4 includes both low power circuitry and high power circuitry. The present disclosure may be employed in a device that provides either or both of a high power electrical stimulation therapy, such as a high power defibrillation therapy, or a low power electrical stimulation therapy, such a pacing pulse, or both. Accordingly, the components in the operational circuitry 48 may support generation and delivery of either one or both such therapies. For ease of description, this disclosure will describe an operational circuitry 48 that supports only a high power electrical stimulation therapy, such as cardioversion and/or defibrillation stimulation therapy. However, it should be noted that the operational circuitry 48 may also provide defibrillation threshold (DFT) induction therapy or post-shock pacing such as anti-tachycardia pacing (ATP) therapy.

The operational circuitry 48 is provided with at least one or more power source(s) 46 which may include a rechargeable and/or non-rechargeable battery having one or more cells. As described in greater detail below, the power source 46 can assume a wide variety of forms. Similarly, the operational circuitry 48, which includes the low power circuit 60 and the output circuit 56, can include analog and/or digital circuits, can assume a variety of configurations, and is electrically connected to the power source 46.

The output circuit 56 and the low power circuit 60 are typically provided as part of an electronics module associated with the ICD 14. In general terms, the output circuit 56 is configured to deliver an electrical pulse therapy, such as a defibrillation or a cardioversion/defibrillation pulse. In sum, the output circuit 56 is responsible for applying stimulating pulse energy between the various electrodes 28-34 (FIG. 1) of the ICD 14. As is known in the art, the output circuit 56 may be associated with a capacitor bank (not shown) for generating an appropriate output energy, for example in the range of 0.1-40 Joules.

The low power circuit 60 is similarly well known in the art. In general terms, the low power circuit 60 monitors heart activity and signals activation of the output circuit 56 for delivery of an appropriate stimulation therapy. Further, as known in the art, the low power circuit 60 may generate a predetermined series of pulses from the output circuit 56 as part of an overall therapy.

In an embodiment, ICD 14 functions are controlled by means of stored software, firmware and hardware that cooperatively monitor the EGM, determine when a cardioversion or defibrillation shock necessary, and deliver prescribed defibrillation therapies. The schematic diagram of FIG. 4 incorporates circuitry set forth in U.S. Pat. No. 5,188,105 "Apparatus and Method for Treating a Tachyarrhythmia" to Keimel, for example, both incorporated herein by reference in its entirety, for selectively delivering single phase, simultaneous biphasic and sequential biphasic cardioversion-defibrillation stimulation therapy. In an exemplary implementation, ICD 14 may deliver stimulation therapy by employing ICD 14 housing electrode 36 coupled to the terminal HV-A and one or two or three electrodes 30, 32, or 34 disposed posterially and subcutaneously and coupled to the nodes HV-B, S1, and S2 outputs (at terminals 36a, 34a 32a, and 30a respectively) of the output circuit 56.

The circuitry 48 of the present disclosure can be made simpler by adoption of one such cardioversion-defibrillation stimulation therapy waveform for delivery simply between the first and second cardioversion-defibrillation electrodes 36 and 32 coupled to the HV-A and HV-B outputs respectively. Alternatively, the circuit can include only a third electrode 32 and the first and second cardioversion-defibrillation electrodes 36 and 32 can be electrically connected in to the HV-A and the HV-B outputs, respectively, as depicted in FIG. 4. For example, ICD 14 may deliver stimulation therapy employing housing electrode 36 coupled to the terminal HV-A and at least one electrode such as electrode 32 coupled to the node HV-B output (at terminals 36a and 32a, respectively) of the output circuit 56. In alternative embodiments, the ICD 14 may employ additional electrodes such as electrodes 30, 34 coupled to nodes such as S1, S2 (at terminals 30a and 34a, respectively) for sensing or stimulation therapy.

The cardioversion-defibrillation stimulation therapy energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICD 14 using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the waveform used. The ICD 14 of the present disclosure uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation stimulation therapies are only delivered when a malignant tachyarrhythmia, e.g., ventricular fibrillation is detected through processing of the far field cardiac ECG employing one of the available detection algorithms known in the ICD 14 art.

In FIG. 4, pacer timing/sense amplifier circuit 52 processes the far field ECG SENSE signal that is developed across a particular ECG sense vector defined by a selected pair of the electrodes 36, 32, and optionally, electrodes 30, 34 if present as noted above. The selection of the sensing electrode pair is made through a control circuit 54 in a manner to provide the most reliable sensing of the EGM signal of interest, which would be the R wave for patients who are believed to be at risk of ventricular fibrillation leading to sudden death. The far field ECG signals are passed through the control circuit 54 to the input of a sense amplifier in the pacer timing/sense amplifier circuit 52.

Control circuit 54 may comprise one or more microprocessors, Application-Specific Integrated Circuits (ASICs), Digital Signal Processors (DSPs), Field-Programmable Gate Arrays (FPGAs), discrete electronic components, state machines, sensors, and/or other circuitry. Control circuit 54 may operate under the control of programmed instructions such as software and/or firmware instructions stored within a storage device (70). The storage device may include volatile, non-volatile, magnetic, optical, and/or electrical media for storing digital data and programmed instructions, including Random Access Memory (RAM), Read-Only Memory (ROM), Non-Volatile RAM (NVRAM), Electrically Erasable Programmable ROM (EEPROM), flash memory, removable storage devices, and the like. These one or more storage devices 70 may store programs executed by control circuit 54.

Storage devices 70 may likewise store data, which may include, but is not limited to, programmed parameters, patient information, data sensed from the patient, and status information indicating the status of the ICD 14. For instance, the data may include statistical information and other characteristic data about the battery (or cell) that is used to predict charge remaining within the power source 46 of ICD 14 as will be discussed in more detail below. The data may further contain ERI and/or EOL indicators to indicate when replacement operations will be needed. This information may be provided to a clinician or patient via the external device 4.

Detection of a malignant tachyarrhythmia is determined in the control circuit 54 as a function of the intervals between R-wave sense event signals that are output from the pacer timing/sense amplifier circuit 52 to the control circuit 54. Certain steps in the performance of the detection algorithm criteria are cooperatively performed in a microcomputer 50, including stored detection criteria that may be programmed into via a telemetry interface (not shown) conventional in the art.

The microcomputer 50 is generally representative of a processor and associated memory in storage device 70. The memory, for example, may include computer readable instructions that, when executed by processor, cause the operational circuitry and or any other component of the medical device to perform various functions attributed to them. For example, the memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Such memory will typically be non-transitory. The processor, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions attributed to the microcomputer 50 may be embodied as software, firmware, hardware, or any combination thereof.

Data and commands are exchanged between microcomputer 50 and control circuit 54, pacer timing/amplifier circuit 52, and output circuit 56 via a bi-directional data/control bus 61. The pacer timing/amplifier circuit 52 and the control circuit 54 are clocked at a slow clock rate. The microcomputer 50 is normally asleep, but is awakened and operated by a fast clock by interrupts developed by each it-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 52.

The detection algorithms are highly sensitive and specific for the presence or absence of life threatening ventricular arrhythmias, e.g., ventricular tachycardia (V-TACH) and ventricular fibrillation (V-FIB). Detection can be provided via R-R Cycle length instability detection algorithms. In addition, detection algorithms for atrial fibrillation may also be included.

Although the ICD 14 of the present disclosure may rarely be used for an actual sudden death event, the simplicity of design and implementation allows it to be employed in large populations of patients at modest risk with modest cost by medical personnel other than electrophysiologists. Consequently, the ICD 14 of the present disclosure includes the automatic detection and therapy of the most malignant rhythm disorders.

When a malignant tachycardia is detected, high voltage capacitors (not shown) within the output circuit are charged to a pre-programmed voltage level by a charging circuit 58. It is generally considered inefficient to maintain a constant charge at all times on the high voltage capacitors. Instead, charging is initiated when control circuit 54 issues a high voltage charge command delivered to charging circuit 58 and charging is controlled by means of bi-directional signal line(s) from the HV output circuit 56. Without intending to be limiting, the high voltage output capacitors may comprise film, aluminum electrolytic or wet tantalum construction.

Some examples of the high voltage output capacitors are described in commonly assigned U.S. Pat. No. 8,086,312, titled "Capacitors for Medical Devices", issued to Nielsen, which is incorporated herein by reference in its entirety.

The high voltage output capacitors may be charged to very high voltages, e.g., 700-3150V, to be discharged through the body and heart between the selected electrode pairs among first, second, and, optionally, third and/or fourth subcutaneous cardioversion-defibrillation electrodes 36, 32, 30, 32. The details of an exemplary charging circuit 58 and output circuit 56 will be discussed below. The high voltage capacitors are charged by charging circuit 58 and a high frequency, high-voltage transformer. The state of capacitor charge is monitored by circuitry within the output circuit 56 that provides a feedback signal indicative of the voltage to the control circuit 54. Control circuit 54 terminates the high voltage charge command when the received signal matches the programmed capacitor output voltage, i.e., the cardioversion-defibrillation peak shock voltage.

Control circuit 54 then develops a control signal that is applied to the output circuit 56 for triggering the delivery of cardioverting or defibrillating shocks. In this way, control circuitry 54 serves to control operation of the high voltage output stage 56, which delivers high energy cardioversion-defibrillation stimulation therapies between a selected pair or pairs of the first, second, and, optionally, the third and/or fourth cardioversion-defibrillation electrodes 36, 32, coupled to the HV-A, HV-B and optionally electrodes 34, 30 coupled to the S1, S2 terminals as shown in FIG. 4.

Thus, ICD 14 monitors the patient's cardiac status and initiates the delivery of a cardioversion-defibrillation stimulation therapy through a selected pair or pairs of the first, second, third and/or fourth electrodes 36, 32, 34, and 30 in response to detection of a tachyarrhythmia requiring cardioversion-defibrillation.

Typically, the charging cycle of the capacitors takes about five to about thirty seconds, and occurs very infrequently. The ICD 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation stimulation therapy can be stored in RAM for uplink telemetry transmission to an external programmer as is well known in the art to facilitate in diagnosis of the patient's cardiac state.

Housing 14 may include a telemetry circuit (not shown in FIG. 4), so that it is capable of being programmed by means of external device 4 (FIG. 1) via a 2-way telemetry link. Uplink telemetry allows device status and diagnostic/event data to be sent to external programmer for review by the patient's physician. Downlink telemetry allows the external programmer via physician control to allow the programming of device function and the optimization of the detection and therapy for a specific patient. Programmers and telemetry systems suitable for use in the practice of the present disclosure have been well known for many years. Known programmers typically communicate with an implanted device via a bi-directional telemetry link such as Bluetooth®, radio-frequency, near field, or low frequency telemetry link, so that the programmer can transmit control commands and operational parameter values to be received by the implanted device, and so that the implanted device can communicate diagnostic and operational data to the programmer.

Those skilled in the art will appreciate that the various components of the low power circuit 60 i.e., pacer/sense circuit 52, control circuit 54, and microcomputer 50 are illustrated as separate components for ease of discussion. In alternative implementations, the functions attributed to these components 50, 52 and 54 may suitably be performed by a sole component.

Figure 5:
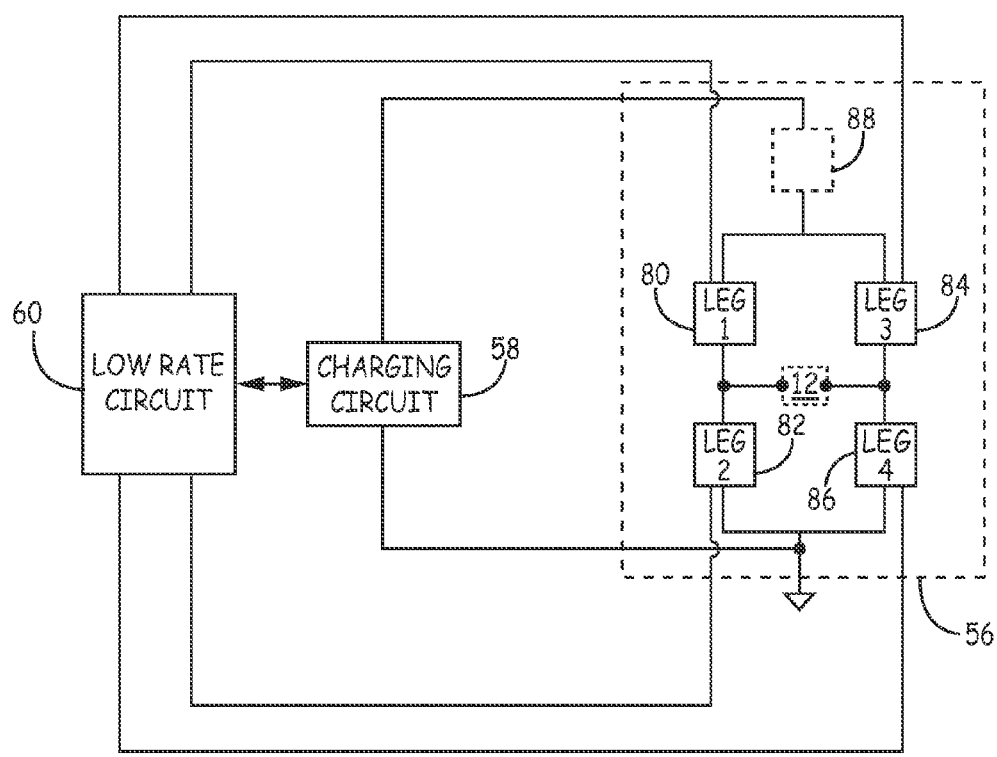
FIG. 5 illustrates an exemplary schematic diagram showing a portion of the operational circuitry of FIG. 4 in accordance with an embodiment of the disclosure.

FIG. 5 illustrates an exemplary schematic showing a portion of the operational circuitry 48 of FIG. 4, in accordance with an embodiment of the disclosure, in greater detail. The output circuit 56 allows the controlled transfer of energy from the energy storage capacitors to the patient 12.

The output circuit 56 includes four legs 80, 82, 84, and 86 that are interconnected. The interconnection of the four legs with legs 80 and 82 being configured in a parallel orientation alongside legs 84 and 86 and a bridge being provided to intersect each of the pair of parallel connected legs. As is shown in FIG. 5, the interconnected legs are arrayed to define a configuration includes a high side and a low side that may resemble a "H". In other words, the four interconnected legs are arrayed having legs 80 and 84 defining the high side and legs 82 and 86 defining the low side.

The intersecting bridge includes HV-A and HV-B terminals that couple the output circuit 56 to the cardioversion electrodes 36 and 32. As previously described, patient 12 is connectable (e.g., using leads/electrodes 36, 32 and any other suitable connections) between terminal HV-A located between the switch 80 and switch 82 and terminal HV-B located between switch 84 and switch 86.

Legs 80 and 84 are coupled to a positive terminal of the energy storage capacitors. An optional discharge switch 88, such as an insulated gate bipolar transistor (IGBT), may be used in the coupling from the legs 80 and 84 to the positive terminal of the energy storage capacitors. Discharge switch 88 may be controlled by control circuit 54 (FIG. 4) that is included within the low power circuit 60 to close and remain in the conducting state during discharge of the capacitors. Leg 82 and 86 are coupled to a negative terminal of the energy storage capacitors. The selection of one or more of the switches 80, 82, 84, 86 under control of control circuit 54 may be used to provide one or more functions. For example, selection of certain switches in one or more configurations may be used to provide one or more types of stimulation pulses, or may be used to provide active or passive recharge, etc.

For example, in accordance with an embodiment, the ICD 14 provides a biphasic defibrillation pulse to the patient in the following manner. With reference to FIG. 5, once the energy storage capacitors are charged to a selected energy level, the switches 80, 86, and 88 are closed so as to provide a path from the capacitors to electrode 36, 32 for the application of a first phase of a defibrillation pulse to the patient 12. The stored energy travels from the positive terminal of the capacitors, through switch 80, across the patient 12, back through switch 86 to the negative terminal of the capacitors. The first phase of the biphasic pulse therefore applies a positive pulse from the electrode 32 to the electrode 36.

After the end of the first phase of the biphasic defibrillation pulse, the switches 88, 84 and 82 are switched on to start the second phase of the biphasic pulse. Switches 84 and 82 provide a path to apply a negative defibrillation pulse to the patient 12. With reference to FIG. 5, the energy travels from the positive terminal of the capacitors, through switch 84, across the electrodes 32, 36 coupled to the patient 12, and out through switch 82 to the negative terminal of the capacitors. The polarity of the second phase of the defibrillation pulse is therefore opposite in polarity to the first phase of the pulse.

As described herein, the low power circuit 60 performs several functions. One of those is to monitor the state of charge of the power source of ICD 14. Another function is to detect a fault condition associated with the power source.

FIG. 6 is a schematic illustrating a portion of the operational circuit 48 of ICD 14. As previously mentioned, the operational circuit 48 includes at least one power source. The power source 46 can assume a wide variety of configurations, as described in the exemplary embodiments below. In an embodiment, the power source 46 may comprise a battery having at least two cells 102a, 102b (collectively "102"). However, it is fully contemplated that power source 46 could contain any other number of cells, such as three, four, six, ten, etc., within volumetric reason so that ICD 14 does not become too large for implantation or uncomfortable to the patient. Notably the first and second cells 102a, 102b (collectively "cells 102") can be formed separate from one another or contained within a singular enclosure. The cells 102 can have any amount of electrode surface area, within reason, to deliver the proper amount of surface energy, such for example, as an electrode surface area of between 45 cm$^2$ and 90 cm$^2$, each. The cells 102 can assume a wide variety of forms as is known in the art, such as a configuration including an anode, a cathode, and an electrolyte. The anode may be formed to include lithium, either in metallic form or ion form for re-chargeable applications. With this in mind, cells 102 may be formed as a spirally wound battery of the type disclosed, for example, in U.S. Pat. No. 5,439,760 to Howard et al. for "High Reliability Electrochemical Cell and Electrode Assembly Therefor" the disclosure of which are hereby incorporated by reference. Cells 102 may alternatively have a spirally wound, or stacked plate, or serpentine electrodes of the type disclosed, for example, in U.S. Pat. No. 5,312,458 to Muffuletto et al. for "Internal Electrode and Assembly Method for Electrochemical Cells;" U.S. Pat. No. 5,549,717 to Takeuchi et al. for "Method of Making Prismatic Cell;" and U.S. Pat. No. 5,147,737 to Post et al. for "Electrochemical Cell With Improved Efficiency Serpentine Electrode;" the disclosures of which are herein incorporated by reference.

Materials for the cathode of cells 102 may be solid in some embodiments and comprise as active components thereof metal oxides such as vanadium oxide, silver vanadium oxide (SVO) or manganese dioxide, as is known in the art. Alternatively, the cathode for cells 102 may also comprise carbon monofluoride and hybrids thereof or any other active electrolytic components and combination. Where SVO is employed for the cathode, the SVO may be of the type known as "combination silver vanadium oxide" (or "CSVO") as disclosed in U.S. Pat. No. 5,221,453 to Crespi et al, although other types of SVO may be employed.

It is to be understood that the cells 102 may be formed from electrochemical systems including, but not limited to, anode/cathode systems such as lithium/silver oxide; lithium/manganese oxide; lithium/$V_2O_5$; lithium/copper silver vanadium oxide; lithium/copper oxide; lithium/lead oxide; lithium/carbon monofluoride; lithium/chromium oxide; lithium/bismuth-containing oxide; lithium/copper sulfate; mixtures of various cathode materials listed above such as a mixture of silver vanadium oxide and carbon monofluoride; and lithium ion rechargeable batteries, to name but a few.

Each of the cells 102 is coupled to a transformer 64 that is included within the output circuit 56 (shown in dashed lines in FIG. 6). In an embodiment, the transformer 64 may be configured as a dual primary transformer having a first primary winding 106a and a second primary winding 106b. In the embodiment, the cell 102a is coupled to the first primary winding 106a and the cell 102b is coupled to the second primary winding 106b.

A first switch 108a is coupled between the first primary winding 106a of the transformer and the cell 102a. A second switch 108b is coupled between the second primary winding 106b of the transformer 64 and the cell 102a. Although not shown in FIG. 6, each of the switches 108a, 108b is coupled to a control circuit, such as control circuit 54 (FIG. 4), which issues control signals (CS1, CS2) to selectively actuate each of the switches 108a, 108b. The control signals may be issued to selectively actuate the switches 108a, 108b separately, simultaneously or in any other desired manner.

Figure 6A:
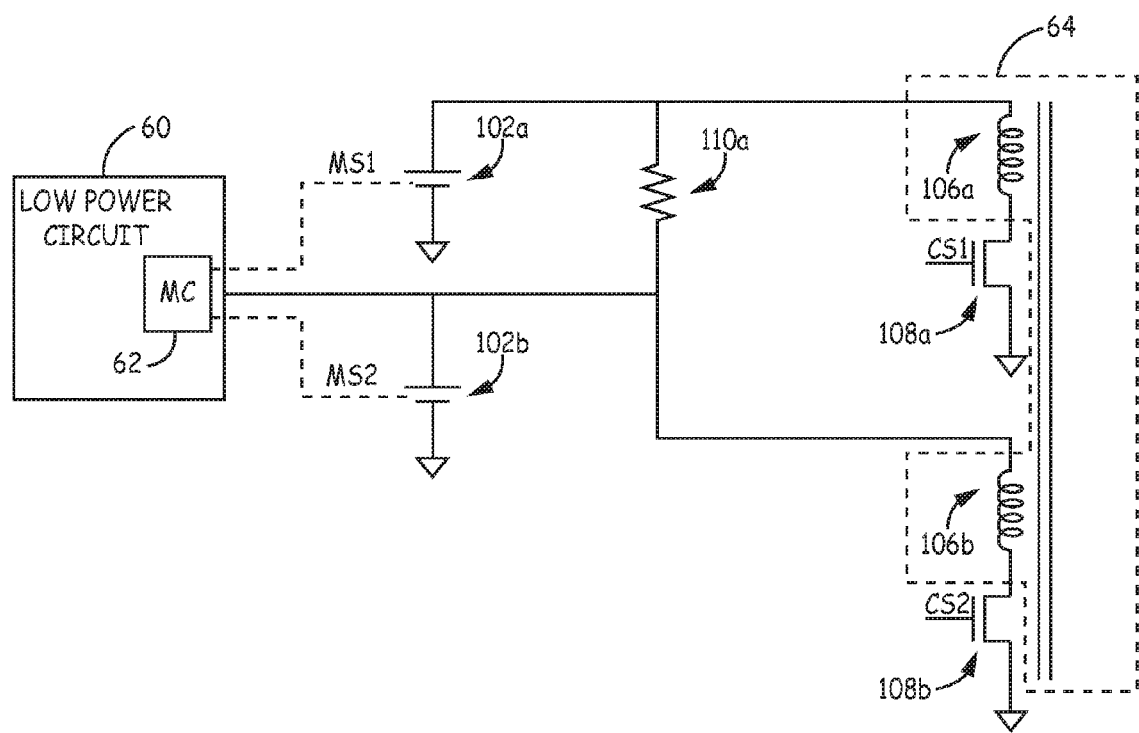
FIG. 6A illustrates an exemplary schematic diagram showing a portion of the operational circuitry of FIG. 4 in accordance with an embodiment of the disclosure.

The cells 102 may be formed with each having a cathode (positive) terminal and an anode (negative) terminal. As is illustrated in the embodiment of FIG. 6A, the cathode terminals of cells 102a, 102b are coupled to the primary winding 106a and the primary winding 106b, respectively, and the anode terminals are both connected to a common node, such as the circuit ground node. In FIG. 6A, the switches 108a, 108b are also coupled to the common node. As such, a first circuit path is defined between the first cell 102a and first primary winding 106a and a second circuit path is defined between the second cell 102b and the primary winding 106b.

Figure 6B:
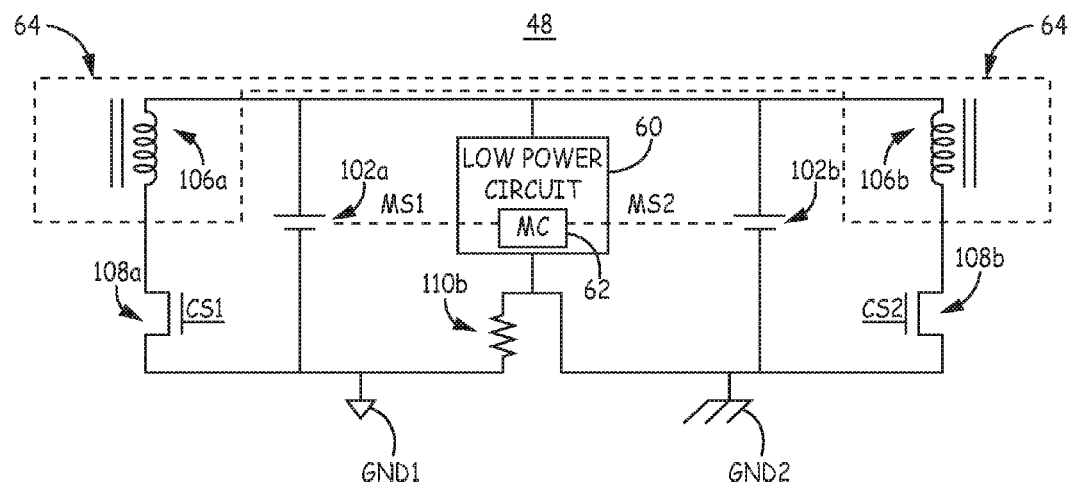
FIG. 6B illustrates an exemplary schematic diagram showing a portion of the operational circuitry of FIG. 4 in accordance with an embodiment of the disclosure.

In the alternative embodiment of FIG. 6B, the cathode terminals of cells 102a, 102b are coupled to the primary winding 106a and the primary winding 106b, respectively, and each of the anode terminals of the cells 102a, 102b is coupled to separate ground nodes such as GND1 and GND2. As such, the switches 108a, 108b in FIG. 6B will be coupled to the separate ground node GND1 and GND2, respectively.

In one embodiment, the switches 108 are simultaneously actuated to a conducting state to enable current to flow from both cells 102 to the transformer 64. The actuation of the first switch 108a into a closed position triggers charge transfer from the first cell 102a to the first primary winding 106a and actuation of the second switch 108b into a closed position triggers charge transfer from the second cell 102b to the second primary winding 106b. In other words, the closing of switch 108a creates a current path for flow of current from the first cell 102a to the transformer 106a while the closing of switch 108b creates a current path for flow of current from the second cell 102b to the transformer 106b.

An isolation circuit 110 (referred to as "110a" in FIG. 6A and "110b" in FIG. 6B) is coupled to the first cell 102a and to the second cell 102b. The cells 102 are arranged in a parallel configuration and the isolation circuit 110 is coupled to one terminal of each of the cells 102a, 102b. As shown in FIG. 6A, the isolation circuit 110a is coupled along the current pathway from the cathode of cell 102a to the low power circuit 60 and transformer 106b. Turning to FIG. 6B, the isolation circuit 110b is coupled along the current pathway from the anode of cell 102a to the low power circuit 60 and the switch 108a.

The low power circuit 60 receives a first level of power from the first and second cells 102, while a high power circuit receives a second level of power (through first and second primary windings 106 of transformer 64) from the first and second cells 102. The first level of power supports low power current operations and is less that the second level of power. The second level of power supports high power current operations. Without intending to be limiting, low power current operations may include operations associated with the analog and digital portions of the operational circuitry 48 while the high power current operations may include generation of electrical stimulation therapy that is delivered to the patient 12 based on a treatment regimen, as is known in the art. In other words, the current delivered by the first and second cells 102 to the low power circuit 60 is less than the current delivered to the high power circuit.

In one embodiment, isolation circuit 110 is configured having an impedance $Z \geq 10 Z_{Battery}$, where Z is the impedance of the effective impedance of the isolation circuit 110 and $Z_{Battery}$ is the effective impedance of an electrical short in cell 102a or cell 102b. In another embodiment, isolation circuit 110 is configured having an impedance $Z \geq 100 Z_{Battery}$ and $Z \ll 10 Z_{Circuit}$, where $Z_{Circuit}$ is the input impedance of low power circuit 60. Generally, Z can be any reasonable value within the specifications above; for example, Z is between 10-100 ohms and $Z_{Battery}$ is about 0.5 ohms. This impedance relationship allows both cell 102a and cell 102b to be discharged uniformly under therapy delivery and sensing conditions. Additionally, skilled artisans appreciate that a battery is defined as including a $Z_{Battery}$ that is less than 0.5 ohm.

The isolation circuit 110 maintains a current isolation between the cells 102 during high power current operations while allowing both batteries to contribute to the current supply to the low power circuitry 60 of the operational circuitry 48 such as 50, 52, and 54 during low power current operations. The high power current operations include the delivery of energy to the transformer 64 to, for example, provide defibrillation therapy. The low power current operations include supply of power to low power circuitry 60. For simplicity of description, the interconnections between the cells 102 and all the components of the operational circuit 48 is not shown. In the event of a failure of one of the cells 102, the isolation circuit 110 isolates the failed battery from the other battery.

After review of this disclosure, those skilled in the art should readily appreciate that if an internal short were to occur, for example, within cell 102a in the absence of isolation circuit 110, then cell 102a would begin to discharge into cell 102b until cell 102a was depleted beyond its operating range. Similarly, if an internal short were to occur, for example, within cell 102b in the absence of isolation circuit 110, then cell 102b would begin to discharge into cell 102a until cell 102b was depleted beyond its operating range.

During the operation of cells 102 in powering low power circuit 60, the only difference in the current path between cell 102a and cell 102b is that the current path for cell 102a must travel through isolation circuit 110. Since cell 102a has a relatively small resistance and the current traveling through isolation circuit 110 is between 10-20 microamps, then the voltage drop across isolation circuit 110 is extremely low, about between 0.1 and 2 millivolts, and therefore cell 102a and cell 102b will deplete at a substantially equal rate while supplying low power circuit 60.

In one embodiment, the isolation circuit 110 may comprise a resistor that is selected having a value that enables current to flow from the first cell 102a to the low power circuitry 60 during low power current operations, but does not allow current to flow during high power current operations. In other words, the resistor value will be large enough to prevent flow of high power current between cell 102a and cell 102b during high power operations such as high clock speed operations like telemetry, but yet low enough to allow flow of low power current between the cell 102a and cell 102b during low power operations such as low clock speed operations like data storage operations. For example, the resistor may have a value in the range of 10 Ohms to 10,000 Ohms. In another example, the resistor may have a value in the range of 500 Ohms to 1,500 Ohms.

The cell 102b is directly coupled to the low power circuitry 60 while the cell 102a is coupled to the low power circuitry 60 through the isolation circuit 110. The low power circuitry 60 may also include monitoring circuitry 62 that is coupled to each of the cells 102 to monitor the energy level of each battery. Any known battery monitoring techniques, such as coulomb counting or a direct voltage measurement may be utilized to monitor the state of charge of the battery. The battery monitoring may be performed through monitoring lines MS1, MS2. In this coupling configuration, the low power circuitry 60 monitors the energy levels in the cells 102 and balances the consumption of charge from each battery by regulating the current drawn from one or both cells 102a, 102b. In other words, low power circuitry 60 controls a rate of battery voltage discharge from each of the first and second cells to maintain a voltage difference between the first and second cells within a predetermined voltage value. For example, the predetermined voltage value may be 500 mV, although any value may be selected, and the cells 102 would be monitored to ensure that the voltage difference does not exceed 500 mV. In the event that the difference exceeds the predetermined voltage value, a balancing may be achieved by preventing consumption from the cell having the lower voltage value until the other cell is depleted such that the difference is within the predetermined voltage value. This balancing effect may be achieved, for example, by issuing a control signal to decouple one of the cells 102a, 102b during low power operations.

The monitoring circuit 62 may monitor the cells 102 by measuring a battery parameter that is, for example, indicative of the residual energy or rate of discharge, of each of the cell 102a and cell 102b. The monitoring circuit 62 may employ techniques that involve computing the indication of the residual energy, or rate of discharge, of the cells 102 utilizing a battery parameter such as the voltage across the terminals of each of the cells 102. In other embodiments, monitoring circuit 62 may alternatively or additionally have the capability to measure a battery parameter such as current flowing from the cells 102.

As will be discussed below, the techniques of the present disclosure involve measurements of a battery parameter of the power source without disconnecting the power source from the circuits that it powers. However, those skilled in the art can appreciate that alternative techniques may be employed that temporarily disconnect the power source from the circuits that it powers to measure the residual energy, or rate of discharge, of the power source. One such method involves measuring an open-circuit voltage across the battery terminals.

Figure 7:
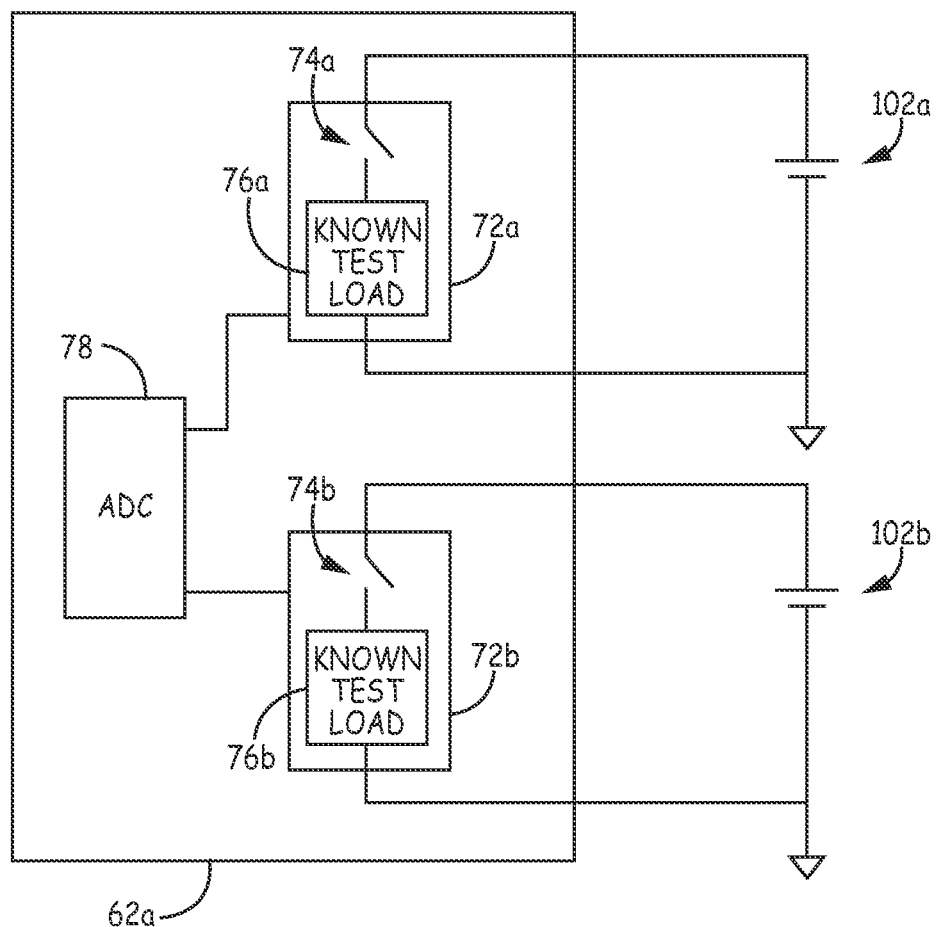
FIG. 7 is a circuit diagram of an embodiment of a monitoring circuit of FIGS. 6A and 6B.

FIG. 7 is a circuit diagram of an embodiment of the monitoring circuit 62 of FIG. 6 coupled to power source 102. Monitoring circuit 62a includes measurement modules 72a and 72b (collectively "measurement modules 72") that are coupled to cell 102a and cell 102b, respectively. Each of the measurement modules 72a, 72b includes a known test load 76a, 76b, coupled to a switch 74a, 74b, respectively. Each of the known test loads 76a, 76b includes a predefined resistance value. In the illustrated embodiment, the measurement modules 72 are configured to measure a battery parameter of each cell 102a and cell 102b. The measured battery parameter may include such parameters as an output voltage of the battery, an internal battery impedance, and a current delivered by the battery.

The control circuit 54 may include instructions for controlling the measurement of the battery parameters by the measurement modules 72. Such instructions may include signals that control the frequency and timing of the measurements. In some embodiments, control circuit 54 may actively cause ICD 14 to discontinue therapy delivery, any communication sessions, and other intermittent activities that draw a sizeable current. Alternatively, control circuit 54 may wait until a time when none of these activities is occurring.

An analog-to-digital converter (ADC) 78 is connected to the measurement modules 72 to measure a battery parameter indicative of the residual energy, or rate of discharge, of the cells 102. A measurement of the battery parameter of the cells 102 is performed by controlling the ADC 78 to measure the voltage or current through the respective known test load 76a or 76b. In the illustrated example of FIG. 7, the measurement of the battery parameter is performed separately for each of cells 102a, 102b. However, alternative embodiments may perform the measurements of the battery parameter of both cells 102 concurrently.

Continuing with the example of FIG. 7, a measurement by the measurement module 72a is performed by closing the switch 74a, which completes the circuit path from the cell 102a though the known test load 76a. Upon closing the switch 74a, the ADC 78 may obtain a value that is representative of the voltage across the known test load 76a. Alternatively, the ADC 78 may obtain a value that is representative of the current flow through the known test load 76a. The control circuit 54 will include instructions to control the timing of the closing of the switch 74a as well as the measurement of the voltage or current by the ADC 78.

The value obtained by the ADC 78 may be a digital representation of the measured voltage across the known load 76a or current through the known load 76a. The microcomputer 50 receives the value of the voltage or current measured by the ADC 78 and this value may, in turn, be provided to one or more external device(s) 4, such as via a telemetry uplink session.

The measurement module 72b may be operated in a manner similar to that described above with respect to measurement module 72a to obtain a battery parameter that is indicative of the residual charge, or rate of discharge, of cell 102b.

Those skilled in the art will appreciate that in alternative embodiments, the monitoring circuit 62a may be implemented with additional components or circuitry.

Figure 8:
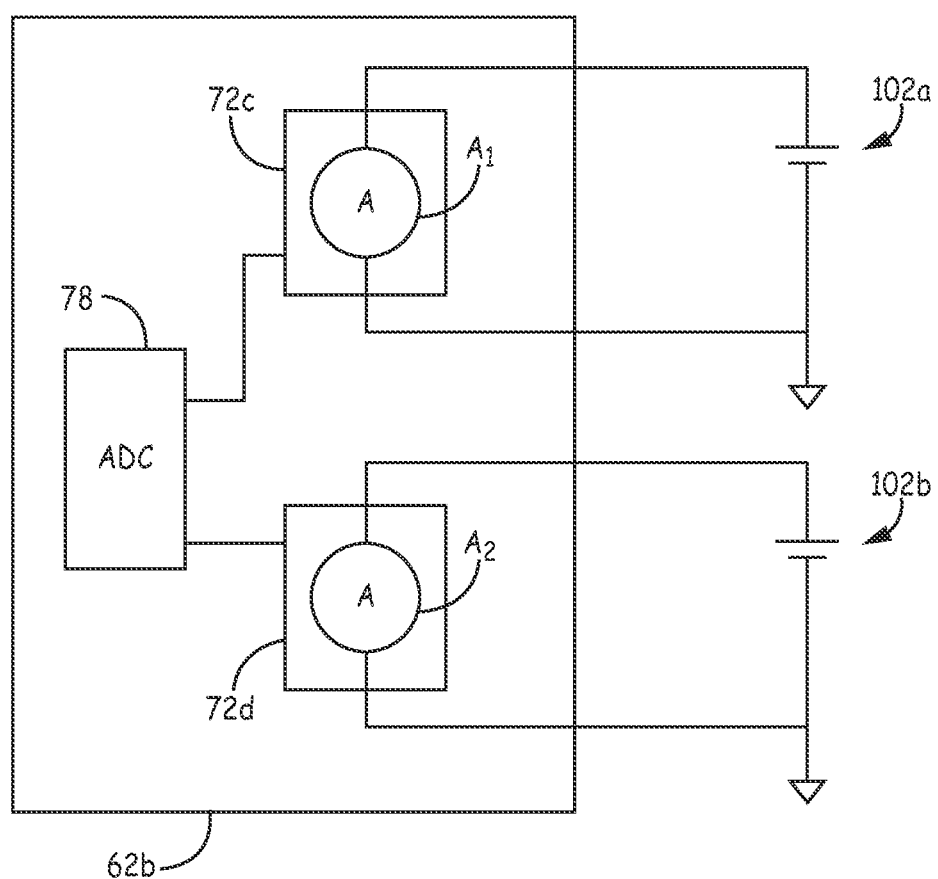
FIG. 8 illustrates an alternative embodiment of the monitoring circuit of FIGS. 6A and 6B.
Figure 9:
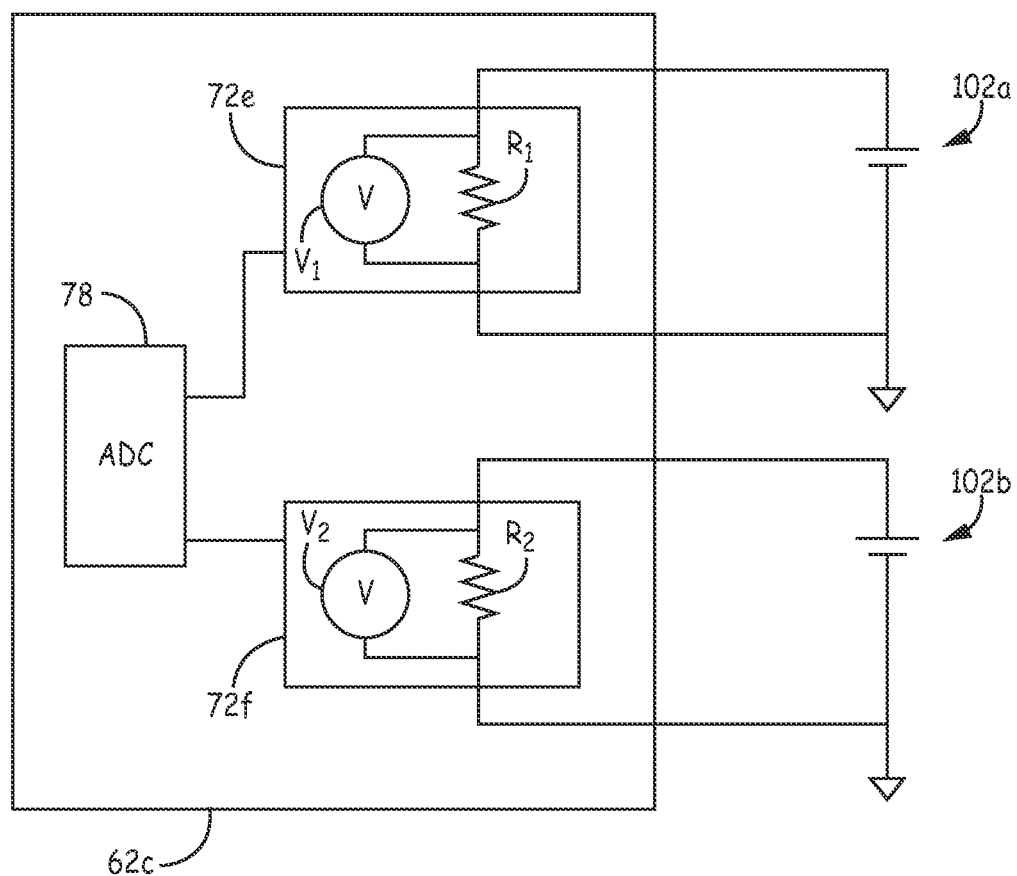
FIG. 9 illustrates an alternative embodiment of the monitoring circuit of FIGS. 6A and 6B.

FIGS. 8 and 9 illustrate alternative embodiments of the monitoring circuit 62 of FIG. 6 being coupled to power source 102 to measure a battery parameter. In FIG. 8, the monitoring circuit 62b includes measurement module 72c that is connected to the cell 102a and measurement module 72d that is connected to the cell 102b. The measurement modules 72c, 72d are operable to measure a value that is indicative of the residual charge, or rate of discharge, of the cells 102a, 102b, respectively. In FIG. 8, the value may be a current measured by the current measurement modules A1, A2.

Turning to FIG. 9, the monitoring circuit 62c includes measurement module 72e that is connected to the cell 102a and measurement module 72f that is connected to the cell 102b. Each of the measurement modules 72e, 72f includes a resistor R1, R2, respectively, that is connected in series to cell 102a, cell 102b, respectively. Each of the measurement modules 72e, 72f also includes voltage measurement module V1, V2, respectively, that measures the voltage across the respective resistor R1, R2. In this configuration, no switches are needed to allow the voltage across the resistor to be measured. The measurement modules 72e, 72f are operable to measure a value that is indicative of the residual charge, or rate of discharge, of the cells 102a, 102b, respectively. In this example, the value corresponds to a closed circuit voltage of the cell 102a or cell 102b. Thus, many alternatives are available for use as measurement circuit 72.

With reference now to FIGS. 7, 8, and 9, the value(s) measured by the monitoring circuits 62a, 62b, 62c, which is representative of the current and/or voltage, is provided to the microcomputer 50 and the measured value(s) may, in turn, be provided to one or more external device(s) 4, such as via a telemetry uplink session.

As may be appreciated, some processing of the measured values may be needed to obtain a processed value or parameter that represents the residual energy or rate of discharge of each battery. For instance, a value of a battery parameter that is obtained by monitoring circuit 62 may be received by microcomputer 50 for processing to yield a processed value that is representative of a range of values corresponding to the capacity of each of the cells 102. The microcomputer 50 may utilize the processed values to determine whether there is an imbalance in the depth of discharge of each of the cells 102, and correspondingly an imbalance in the residual charge within the cells 102.

Additionally, microcomputer 50 may also determine time remaining until some action is required. Such an action may include the remaining time until an ERI or EOL must be activated based on the processed value. In some instances, an action may be taken as a result of an identified difference in the depth of discharge and/or a time-remaining determination. For instance, an ERI or EOL indication may be activated, or a warning may be issued that there is a detected imbalance in the depth of discharge of the cells 102.

An imbalance in the residual charge of cells 102a, 102b may also be indicative of a fault condition associated with at least one of the cells 102a, 102b. For example, the imbalance in the residual energy may occur as a result of a high resistance, a loss of capacity, and a high self-discharge associated with one of the cells 102a, 102b.

In one embodiment, the determination of the charge imbalance may be computed by microcomputer 50 though a comparison of the processed values for each of the cells 102a, 102b to obtain the relative difference in the processed values for each of the cells 102a, 102b. In alternative embodiments, the processed value obtained for each of the cells 102 is compared to a predetermined value stored in memory 70. The microcomputer 50 assesses the presence of a fault condition based on the results of the comparison. For example, if the results indicate a relative difference between the processed value for a given battery and the predetermined value that exceeds a predetermined threshold value (e.g., five percent), then the battery may be deemed to be faulty. In a similar manner, the result of the comparison of the relative difference between the processed value for cell 102a and the processed value for cell 102b may be evaluated to determine whether the values are within a predetermined threshold value (e.g., five percent). If so, then the one of cells 102a, 102b with the lower value may be deemed to be faulty.

The predetermined value that is utilized for the comparison to the processed value corresponds to battery characteristic data for the specific type of cells 102. Such battery characteristic data may be derived empirically based on measurements made on multiple batteries that are of the same battery type and make up as the power source 46. This data may be provided in graphical format as exemplified in U.S. Pat. No. 8,612,167, which is entitled "Estimating Remaining Battery Service Life in an Implantable Medical Device" to Schmidt et al., and U.S. Pat. No. 6,671,552, which is entitled "System and Method for Determining Remaining Battery Life for an Implantable Medical Device" to Merritt et al., all of which are incorporated herein by reference in their entirety. Alternatively, this type of data may be presented in tabular format (or some other format). Some or all of this data may reside within the memory of storage device(s) 70. Alternatively or additionally, some or all of this data may reside within storage device(s) of an external device 4 (FIG. 1).

In accordance with the foregoing, some notification containing status and other data may be provided to a user via external device 4 (FIG. 4). This notification may be provided as a text message, an icon, and/or some other visual indication. Alternatively or additionally, the notification may include an audio signal such as a warning tone or a message delivered via electronically-synthesized speech. Further, a tactile feedback, such as a vibration, may also be provided. The status and/or data communicated in this manner may include the value derived for the residual energy of each of the cells 102a, 102b, the time remaining until an action is required, information pertaining to the action that is required, or any other information pertaining to the measured values that will aid a user in preparing for an action to be taken concerning the residual energy in cells 102.

Providing software, firmware and hardware to accomplish the present invention, given the disclosure herein, is within the abilities of one of skill in the art. For the sake of brevity, conventional techniques related to ventricular/atrial pressure sensing, signal processing, telemetry, and other functional aspects of the systems (and the individual operating components of the systems) may not be described in detail herein. The connecting lines shown in the various figures contained herein are intended to represent example functional relationships and/or physical couplings between the various elements. It should be noted that many alternative or additional functional relationships or physical connections may be present in an embodiment of the subject matter.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

For example, the following Items are illustrative of further embodiments of the disclosure:

Item 1. An implantable medical device, comprising:
operational circuitry having a low power circuit segment and a high power circuit segment;
a power source having at least first and second cells coupled to the operational circuitry;
an isolation circuit connected to the first and second cells and operable to couple the first and second cells in a safe parallel orientation, wherein the first and second cells are configured in a first configuration to deliver energy to the low power circuit segment and in a second configuration that is different from the first configuration to deliver energy to the high power circuit segment; and
a monitoring circuit coupled to the power source and operable to compute a first value corresponding to a parameter of the first cell and a second value corresponding to the parameter of the second cell, wherein the monitoring circuit evaluates the first value and the second value to detect a fault condition associated with at least one of the first and second cells.

Item 2. The implantable medical device of item 1, wherein the isolation circuit is configured having an impedance that permits the isolation circuit to be bypassed during delivery of energy from the first and second cells to the high power circuit segment.

Item 3. The implantable medical device of any one of items 1-2, wherein the monitoring circuit measures a current flowing through from each of the first and second cells to compute the first and second values.

Item 4. The implantable medical device of any one of items 1-3, wherein the monitoring circuit measures an output voltage of each of the first and second cells to compute the first and second values.

Item 5. The implantable medical device of any one of items 1-4, wherein the monitoring circuit measures an electrical property corresponding to an amount of residual energy within each of the first and second cells to compute the first and second values.

Item 6. The implantable medical device of any one of items 1-2, wherein the parameter comprises at least one of an output voltage, an internal cell impedance, and a current delivered across a load coupled to each of the first and second cells.

Item 7. The implantable medical device of any one of items 1-6, wherein the evaluation by the monitoring circuit comprises comparing the first value to the second value to detect the fault condition associated with at least one of the first and second cells.

Item 8. The implantable medical device of any one of items 1-7, wherein the fault condition comprises at least one of a high resistance, a loss of capacity, and a high self-discharge.

Item 9. The implantable medical device of any one of items 1-8, further comprising a communications module operable to issue an alert based on the detection of the fault condition associated with at least one of the first and second cells.

Item 10. The implantable medical device of any one of items 1-9, wherein the first value and the second value are converted into an estimate of remaining longevity of the power source based on a comparison of the first and second values to a predetermined value.

Item 11. The implantable medical device of item 10, wherein the predetermined value is stored in a look-up table.

Item 12. The implantable medical device of any one of items 1-11, further comprising a control circuit operable to selectively configure the first and second cells in the first and second configurations,
wherein only one of the first cell or second cell delivers energy to the low power circuit segment in the first configuration, and wherein the first cell and second cell synchronously deliver energy to the high power circuit segment during the second configuration.

Item 13. The implantable medical device of any one of items 1-12, further comprising a memory having a look-up table including at least one predetermined value, wherein the evaluation by the monitoring circuit comprises comparing the first value to the second value to detect the fault condition associated with at least one of the first and second cells.

Item 14. The implantable medical device of any one of items 1-13, further comprising a voltage converter for converting the first value and the second value into an estimate of remaining longevity of the power source.

Item 15. The implantable medical device of any one of items 1-14, wherein the monitoring circuit further compares the first value to the second value to estimate a remaining longevity of the power source.

Item 16. An implantable medical device, comprising:
operational circuitry having a low power circuit segment and a high power circuit segment;
a power source having at least first and second cells coupled to the operational circuitry;
means for isolating the first cell from the second cell to configure the first and second cells in a safe parallel orientation, wherein the first and second cells are arranged in a first configuration to deliver energy to the low power circuit segment and a second configuration that is different from the first configuration to deliver energy to the high power circuit segment; and
means for monitoring the power source to compute a first value corresponding to a parameter of the first cell and a second value corresponding to the parameter of the second cell, wherein the monitoring circuit evaluates the first value and the second value to detect a fault condition associated with at least one of the first and second cells.

Item 17. The implantable medical device of item 16, further comprising means for selectively configuring the first and second batteries in one of the first and second configurations, wherein in the first configuration, only one of the first cell or second cell delivers energy to the low power circuit segment, and
wherein in the second configuration, the first cell and second cell synchronously deliver energy to the high power circuit segment.

Item 18. The implantable medical device of any one of items 16-17, wherein the means for isolation is configured having an impedance that permits the first cell to be isolated from the second cell during delivery of energy to the low power circuit segment in the first configuration, and
wherein the impedance permits the means for isolation to be bypassed during delivery of energy from the power source to the high power circuit segment in the second configuration.

Item 19. The implantable medical device of any one of items 16-18, wherein the evaluation by the means for monitoring comprises comparing the first value to the second value to detect the fault condition.

Item 20. The implantable medical device of any one of items 16-19, further comprising storage means including at least one predetermined value, wherein the means for monitoring compares the at least one predetermined value to the first and second values to detect the fault condition.

Item 21. The implantable medical device of any one of items 16-20, wherein monitoring means further compares the first value to the second value to estimate a remaining longevity of the power source.

Item 22. The implantable medical device of any one of items 16-21, wherein the monitoring means measures a current flowing through from each of the first and second batteries to compute the first and second values.

What is claimed is:

1. An implantable medical device, comprising:
operational circuitry comprising a low power circuit and a high power output circuit, wherein the high power output circuit comprises a transformer having a first primary winding and a second primary winding;
a power source comprising at least first and second cells coupled to the operational circuitry, the first cell being coupled to the first primary winding and the second cell being coupled to the second primary winding;
an isolation circuit connected to the first and second cells to maintain current isolation between the first and second cells during delivery of energy to the high power output circuit during high power operation while allowing both the first and second cells to contribute current to power the low power circuit during low power operation, wherein the first and second cells are configured in a first configuration to deliver energy to the low power circuit and in a second configuration that is different from the first configuration to deliver energy to the high power output circuit;
a control circuit operable to selectively configure the first and second cells in the first and second configurations, wherein the first cell and second cell simultaneously deliver energy to the high power output circuit when configured in the second configuration; and
a monitoring circuit coupled to the power source to monitor an energy level of each of the first cell and the second cell and operable to compute a first value corresponding to a parameter of the first cell and a second value corresponding to the parameter of the second cell, wherein the monitoring circuit evaluates the first value and the second value to detect a fault condition associated with at least one of the first and second cells.

2. The implantable medical device of claim 1, wherein the isolation circuit is configured having an impedance that permits the isolation circuit to be bypassed during delivery of energy from the first and second cells to the high power output circuit.

3. The implantable medical device of claim 1, wherein the monitoring circuit measures a current flowing through each of the first and second cells to compute the first and second values.

4. The implantable medical device of claim 1, wherein the monitoring circuit measures an output voltage of each of the first and second cells to compute the first and second values.

5. The implantable medical device of claim 1, wherein the parameter corresponds to an amount of residual energy within each of the first and second cells.

6. The implantable medical device of claim 1, wherein the parameter comprises at least one of an output voltage, an internal cell impedance, and a current delivered across a load coupled to each of the first and second cells.

7. The implantable medical device of claim 1, wherein the evaluation by the monitoring circuit comprises comparing the first value to the second value to detect the fault condition associated with at least one of the first and second cells.

8. The implantable medical device of claim 1, wherein the fault condition comprises at least one of a high resistance, a loss of capacity, and a high self-discharge.

9. The implantable medical device of claim 1, further comprising a communications module operable to issue an alert based on the detection of the fault condition associated with at least one of the first and second cells.

10. The implantable medical device of claim 1, wherein the first value and the second value are converted into an estimate of remaining longevity of the power source based on a comparison of the first and second values to a predetermined value.

11. The implantable medical device of claim 10, wherein the predetermined value is stored in a look-up table.

12. The implantable medical device of claim 1, further comprising a memory having a look-up table including at least one predetermined value, wherein the evaluation by the monitoring circuit comprises comparing each of the first and second values to the predetermined value to detect the fault condition associated with at least one of the first and second cells.

13. The implantable medical device of claim 1, further comprising a voltage converter for converting the first value and the second value into an estimate of remaining longevity of the power source.

14. The implantable medical device of claim 1, wherein the monitoring circuit further compares the first value to the second value to estimate a remaining longevity of the power source.

15. An implantable medical device, comprising:
operational circuitry comprising a low power circuit and a high power output circuit, wherein the high power output circuit comprises a transformer having a first primary winding and a second primary winding;
a power source comprising at least first and second cells coupled to the operational circuitry, the first cell being coupled to the first primary winding and the second cell being coupled to the second primary winding;
means for isolating the first cell from the second cell to maintain current isolation between the first and second cells during delivery of energy to the high power output circuit during high power operation while allowing both the first and second cells to contribute current to power the low power circuit during low power operation, wherein the first and second cells are arranged in a first configuration to deliver energy to the low power circuit and a second configuration that is different from the first configuration to deliver energy to the high power output circuit;
means for selectively configuring the first and second cells in the first and second configurations, wherein the first cell and second cell simultaneously deliver energy to the high power output circuit when configured in the second configuration; and
means for monitoring an energy level of the power source to compute a first value corresponding to a parameter of the first cell and a second value corresponding to the parameter of the second cell, wherein the monitoring circuit evaluates the first value and the second value to detect a fault condition associated with at least one of the first and second cells.

16. The implantable medical device of claim 15, wherein in the first configuration, only one of the first cell or second cell delivers energy to the low power circuit, and
wherein in the second configuration, the first cell and second cell simultaneously deliver energy to the high power output circuit.

17. The implantable medical device of claim 15, wherein the means for isolation is configured having an impedance that permits the first cell to be isolated from the second cell during delivery of energy to the low power circuit in the first configuration, and wherein the impedance permits the means for isolation to be bypassed during delivery of energy from the power source to the high power output circuit in the second configuration.

18. The implantable medical device of claim 15, wherein the evaluation by the means for monitoring comprises comparing the first value to the second value to detect the fault condition.

19. The implantable medical device of claim 15, further comprising storage means including at least one predetermined value, wherein the means for monitoring compares the at least one predetermined value to the first and second values to detect the fault condition.

20. The implantable medical device of claim 15, wherein monitoring means further compares the first value to the second value to estimate a remaining longevity of the power source.

21. The implantable medical device of claim 15, wherein the monitoring means measures a current flowing through from each of the first and second cells to compute the first and second values.

* * * * *